(12) United States Patent
Gentile et al.

(10) Patent No.: US 7,250,152 B2
(45) Date of Patent: Jul. 31, 2007

(54) SUPERCRITICAL FLUIDS PROCESSING: PREPARATION OF PROTEIN MICROPARTICLES AND THEIR STABLILISATION

(75) Inventors: Marco Gentile, L'Aquila (IT); Cesare Di Palma, L'Aquila (IT); Maria Candida Cesta, L'Aquila (IT)

(73) Assignee: Dompé pha.r.ma S.p.A., L'Aqila (IT)

( * ) Notice: Subject to any disclaimer, the term of this patent is extended or adjusted under 35 U.S.C. 154(b) by 0 days.

(21) Appl. No.: 10/493,256

(22) PCT Filed: Oct. 21, 2002

(86) PCT No.: PCT/EP02/11761

§ 371 (c)(1),
(2), (4) Date: Sep. 13, 2004

(87) PCT Pub. No.: WO03/035673

PCT Pub. Date: May 1, 2003

(65) Prior Publication Data
US 2005/0065063 A1 Mar. 24, 2005

(30) Foreign Application Priority Data
Oct. 22, 2001 (EP) ................... 01125048

(51) Int. Cl.
*A61K 51/00* (2006.01)
(52) U.S. Cl. .................................... 424/1.13
(58) Field of Classification Search ................ 424/1.13
See application file for complete search history.

(56) References Cited
U.S. PATENT DOCUMENTS

| 5,770,559 A | 6/1998 | Randolph et al. |
| 5,874,029 A | 2/1999 | Said et al. |
| 6,063,910 A | 5/2000 | Debenedetti et al. |
| 6,630,121 B1 * | 10/2003 | Sievers et al. ............. 424/1.13 |
| 2002/0073511 A1 * | 6/2002 | Hanna et al. ............. 23/295 R |

FOREIGN PATENT DOCUMENTS

| EP | 0677332 | 10/1995 |
| EP | 0767702 | 12/1998 |
| WO | WO 95/01221 | 1/1995 |
| WO | WO 96/00610 | 1/1996 |
| WO | WO 98/36825 | 8/1998 |
| WO | WO 99/59710 | 11/1999 |
| WO | WO 00/69887 | 11/2000 |
| WO | WO 00/75281 | 12/2000 |
| WO | WO 01/03821 | 1/2001 |
| WO | WO 01/15664 | 3/2001 |

OTHER PUBLICATIONS

Ford et al. The effect of carbohydrate additives in the freeze-drying of alkaline phosphatase. Journal of Pharmacy and Pharmacology. 1993. 45, 2, 86-93.*
Ford, "The effect of carbohydrate additives in the freezw-drying of alkaline phosphatase" Journal of Pharmacy and Pharamcology 45(2):86-93 1993.
Sellers et al., Journal of Pharmaceitical Sciences, Jun. 2001, 90(6):785-797.
Sellers et al., Book of Abstracts, 219th ACS National Meeting, San Francisco, CA, Mar. 26-30, 2000, Entry 173.
Jung et al., "Particle design using supercritical fluids: Literature and patent survey," *Journal of Supercritical Fluids*, 20(3):179-219, Aug. 2001.
Winters, et al., "Long-Term and High-Temperature Storage of Supercritically-Processed Microparticulate Protein Powders," Pharmaceutical Research, vol. 14, No. 10, 1977, pp. 1370-1378.

* cited by examiner

*Primary Examiner*—Karen Cochrane Carlson
*Assistant Examiner*—Suzanne M. Noakes
(74) *Attorney, Agent, or Firm*—Needle & Rosenberg (57) ABSTRACT

A process for the co-precipitation of a substance with a stabilizer therefor, by a gas anti solvent process comprising introducing into a particle formation vessel a supercritical fluid pure or mixed with a modifier; and a solution comprising said substance and said stabilizer dissolved in a solvent; so as said solvent is extracted from the solution by said supercritical fluid and co-precipitation of the substance and stabilizer occurs. The process may be carried out using an apparatus, for example, shown in FIG. 1, comprising a particle formation vessel (22) and a nozzle (27) having a central orifice (39) serving to introduce a solution of the substance and a plurality of outer orifices (41) serving to carry a flow of supercritical fluid into the particle formation vessel (22), such that the solvent is extracted from the solution by the supercritical fluid and precipitation of micron sized particles of the substance/stabilizer occurs.

18 Claims, 7 Drawing Sheets

Thermal analysis of supercritical CO2 co-precipitated lysozyme/trehalose powders.
a: pure trehalose; b: lysozyme/trehalose 1:5 ratio; c: pure lysozyme; d: lysozyme/trehalose 4:1 ratio; e: lysozyme/trehalose 2:1 ratio; f: lysozyme/trehalose 1:2 ratio.

SUPERCRITICAL FLUIDS PROCESSING: PREPARATION OF PROTEIN MICROPARTICLES AND THEIR STABLILISATION

CROSS REFERENCE TO RELATED APPLICATIONS

The present application claims priority to European Application No. 01125048.7, filed Oct. 22, 2001, which application is incorporated herein fully by this reference.

FIELD OF THE INVENTION

The present invention relates to a method for protein and polypeptide precipitation by supercritical fluid processing and their protection and stabilisation against denaturation.

BACKGROUND OF THE INVENTION

The need for stable proteins and polypeptides for many applications is continuously increasing. This is particularly pronounced for therapeutic proteins in the pharmaceutical field. For the ease of both manufacturers and final users aqueous protein solutions are often the preferred form of administration. Moreover this is their common natural form that allows hydrated, three-dimensional folded complex formation. This conformation is generally reported as tertiary structure and its integrity is of vital importance for maintaining the biological activity of proteins. The irreversible loss of tertiary structure of proteins is referred as denaturation and causes inactivation. Because proteins and polypeptides in solution are exposed to many stresses which can cause physical (denaturation) and chemical (i.e. reactions such as hydrolysis, deamidation etc. . . . ) degradation, very often the development of liquid formulations is precluded. Presently, the most common way to achieve protein stability is the removal of water by suitable processes such as freeze-drying or spray-drying. However, both of these techniques (ref. "Formulation and Delivery of Proteins and Peptides" J. L. Cleland and R. Lan ger American Chemical Society, Washington, D.C. 1994) can induce protein unfolding. In particular with regard to lyophilisation protein unfolding can occur either during the initial freezing step or during acute dehydration by sublimation.

Concerning spray drying, thermal degradation, low efficiency, low yield and high levels of residual moisture are the main limitations of the technique.

Another problem is the difference in long term stability of analogous formulations obtained by different drying processes. In fact, depending on the dehydration method, the protein may assume different three-dimensional structures with the same initial biological activity but different shelf life.

The stabilising effect of carbohydrates and in particular of trehalose on proteins during freezing and dehydration is well documented ("Formulation and Delivery of Proteins and Peptides" J. L. Cleland and R. Lan ger American Chemical Society, Washington, D.C. 1994 and "Freeze-Drying/Lyophilization of Pharmaceutical and Biological Products" L. Rey and J. C. May, Marcel Dekker, Inc. New York 1999). Although many sugars can prevent protein damage during dehydration, the products often have a short shelf life at room temperature due to the Maillard reaction. Stability at room temperature can be improved using non reducing sugars such as sucrose and trehalose.

British Patent Application GB 2009198 discloses lyophilisation of meningococcal polysaccharide and trehalose; GB 2126588 discloses the stabilisation of tumour necrosis factor (TNF) to lyophilisation and freezing by including either a non-ionic surfactant or trehalose (or another sugar); and Japanese Patent Application J 58074696 discloses the freeze-drying of ATP in presence of trehalose.

Preparations of alkaline phosphatase containing trehalose are reported to maintain their activity after freeze-drying and to maintain about 70% of the initial activity after 84 days/ storage at 45° C. (A. W. Ford et Al., J. Pharm. Pharmacol. 1993, 45: 86-93). Although lyophilisation is still the main process used for drying proteins, several precautions must be taken in order to avoid the damage that severe stressing phases such as freeze-thawing and drying can cause. In fact, during the first step in freeze-dried protein formulation, a correct choice of conditions (pH, ionic strength, presence of stabilisers, etc. . . . ) guarantees the best protection against protein unfolding and inactivation. Many excipients such as sugars, aminoacids, polymers, surfactants specific ligands (substrates, co-factors, allosteric modifiers etc. . . . ) are known to stabilise proteins during freeze-drying and have been named "lyoprotectants". Among them, carbohydrates and in particular disaccharides such as sucrose and trehalose have been widely studied. The stabilising mechanism of these compounds as well as other stabilisers has not been completely clarified. However, an effective lyoprotectant must maintain stability during both freeze-thawing and drying. Since the protein environment is aqueous during much of the freezing process, solutes that stabilise the native conformation in aqueous solutions are very often effective as protein cryoprotectants. Carbohydrates and some aminoacids are examples. Arakawa et Al. (J. Pharm. Res. 1991, 8, 285-291) reported that such solutes tend to be excluded from the surface of protein while in aqueous solution. The thermodynamic consequence of such phenomenon is the stabilisation of protein native conformation.

Stability during drying and storage is best explained by both the water substitution and the vitrification hypotheses. The first states that stabilisers interact with the protein as water does by replacing the removed water and accounts for the thermodynamic control of drying process. The latter states that stabilisers are good glass formers and remain amorphous during and after drying so that they mechanically immobilise proteins inside a glassy matrix. This is a purely kinetic argument that applies equally well to both drying and storage stability. ("Freeze-Drying/Lyophilization of Pharmaceutical and Biological Products" L. Rey and J. C. May, Marcel Dekker, Inc. New York 1999).

Hence, referring to the above stabilisation hypothesis of dried proteins, it can be postulated that vitrification is one of the main issues for long term stability. The use of spray-drying for protein desiccation has been less investigated. Although fine amorphous particles can be produced, this process requires warm air as a drying force that can lead to protein thermal degradation. Moreover, low efficiency, low yield and high levels of residual moisture are other limitations.

Another reported technique for drying proteins which should avoid inactivation is air dehydration at room temperature. U.S. Pat. No. 4,891,319 of Quadrant Bioresources Ltd (UK) discloses the preservation of several proteins and other macromolecules at 37-40° C. by drying in presence of trehalose at atmospheric pressure.

The use of supercritical fluid technology has also been reported as a useful method for obtaining proteins as dry fine micro-particles. The main advantages of this technique are the possibility of maintaining the protein in a favourable aqueous environment before a rapid precipitation in order to minimise denaturation and the process length which is shorter than freeze-drying and less expensive.

S. P. Sellers et Al. (J. Pharm. Sci., 2001, 90, 785-797) report a dehydration method for protein powder production based on supercritical $CO_2$-assisted nebulization. This technique can be assimilated to spray-drying; in fact supercritical $CO_2$ is used for enhancing solution nebulization and not as an anti-solvent solvent for solute precipitation. The GAS (Gas Anti-Solvent recrystallization) process to form protein microparticles is reported by Debenedetti (U.S. Pat. No. 6,063,910). In this case the protein solution is sprayed through a laser drilled platinum disc with a diameter of 20 µm and a length of 240 µm inside the particle formation vessel previously filled by supercritical fluid which is introduced by a different inlet. This technique has been used to form particles of catalase and insulin (0.01% w/v) from ethanol/water (9:1 v/v) solutions using carbon dioxide as the supercritical fluid. In this process, the supercritical fluid inlet is not optimized: the solution injection occurs in an almost static atmosphere of supercritical fluid, with low turbulence. Hanna M. and York P. (WO96/00610) proposed a new method and a new apparatus to obtain very small particles by a specific supercritical fluid technique named SEDS (Solution Enhanced Dispersion by Supercritical Solution).

The process is based on a new coaxial nozzle: the solution expands through a capillary inlet, supercritical fluid expands through an external coaxial pathway with a conical shaped end. The mixing between supercritical fluid and solution occurs in the conical zone. They also propose the use of a three way nozzle: a modifier can be fed in order to improve the mixing.

They applied the SEDS technology to precipitation of small particles of water soluble compounds, such as sugars (Lactose, Maltose, Trehalose and Sucrose) and proteins (R-TEM beta-lactamase). Co-precipitation of proteins and stabilisers is not mentioned nor exemplified therein.

Moreover, the same inventors (WO01/03821) describe an improved precipitation method using the same apparatus but feeding to the particle formation vessel a supercritical fluid and two immiscible solvents. This method allows co-precipitation of two or more solutes dissolved in the two immiscible solvents. The fluids inlet is formed by a coaxial nozzle wherein contact between the two solvents occurs shortly before their dispersion by the supercritical anti-solvent, avoiding the precipitation solutes inside the nozzle. However this method permits the formation of homogeneous co-precipitates; it is generally useful when two solutes with different polarity must be processed. Moreover, if this is used for an aqueous solution, the second solvent must be at least partly soluble in water so that it allows the water to disperse in the supercritical anti-solvent. This step is necessary to permit water-soluble solute precipitation. Co-precipitation of proteins and stabilisers is not described in this document.

Walker (WO01/15664) discloses a method for co-formulating an active (preferably a pharmaceutically active) substance and an oligomeric or polymeric excipient in which an amount between 80 and 100% of the active substance is in amorphous as opposed to crystalline form. In these formulations the active substances are more stable compared to the crystalline forms when stored at temperature between 0 and 10° C. Only the co-formulation of a pharmaceutical active substance with an oligomeric or polymeric excipient is disclosed and there is no mention of protein stabilisation in this document. Protein stabilisation is therefore achieved in the art through freeze-drying and spray-drying. The co-precipitation of proteins with stabilisers using supercritical fluids has not been described before and it is the object of the present invention.

We have now found a method of producing stable dry protein microparticles by co-precipitation with a stabiliser using supercritical fluids. Preferred stabilisers are carbohydrates, aminoacids, surfactants and polymers. More preferably the stabilizer is a sugar, most preferably trehalose.

Co-precipitation allows intimate interactions between the protein/stabiliser molecules and an optimal weight/weight ratio exists for each couple protein/stabiliser.

In fact since there is no freeze-thawing there is no need for cryoprotection. Moreover, although the nature of protein/stabiliser interactions has to be better clarified, in the present case the stabiliser plays the essential role of improving storage stability rather than that of retaining protein activity during drying. In fact, precipitation by a supercritical fluid allows by itself protein particle production without denaturation during the drying process.

STATEMENT OF THE INVENTION

The term "supercritical fluid" means a fluid at or above its critical pressure and its critical temperature.

The term "solvent" means a liquid, which is able to form a solution with the protein and the stabiliser.

The term "stabiliser" means a solid pharmaceutical excipient which is able to stabilise, for example, proteins, which is soluble in the solvent and which is substantially insoluble in the supercritical fluid.

The term "modifier" is a substance, preferably a solvent, which enhances the solubility of the "solvent" in the supercritical fluid.

The present invention provides a process for the co-precipitation of a substance with a stabiliser therefor, by a gas anti solvent process comprising introducing into a particle formation vessel a supercritical fluid pure or mixed with a modifier; and a solution comprising said substance and said stabiliser dissolved in a solvent;

so as said solvent is extracted from the solution by said supercritical fluid and co-precipitation of the substance and stabiliser occurs.

Preferably, the solution is introduced into the particle formation vessel mixed with a modifier. The process includes the introduction into a particle formation vessel of a solution or suspension of the substance and the stabiliser and a supercritical fluid. In the particle formation vessel, mixing of the supercritical fluid with the solution and extraction of the solvent by the supercritical fluid occurs so that the solutes (substance and stabiliser) co-precipitate as fine particles. If the solvent is not miscible with the supercritical fluid, the use of a modifier is needed. The modifier is a compound which is soluble both in the solvent and in the supercritical fluid.

Figure 1:
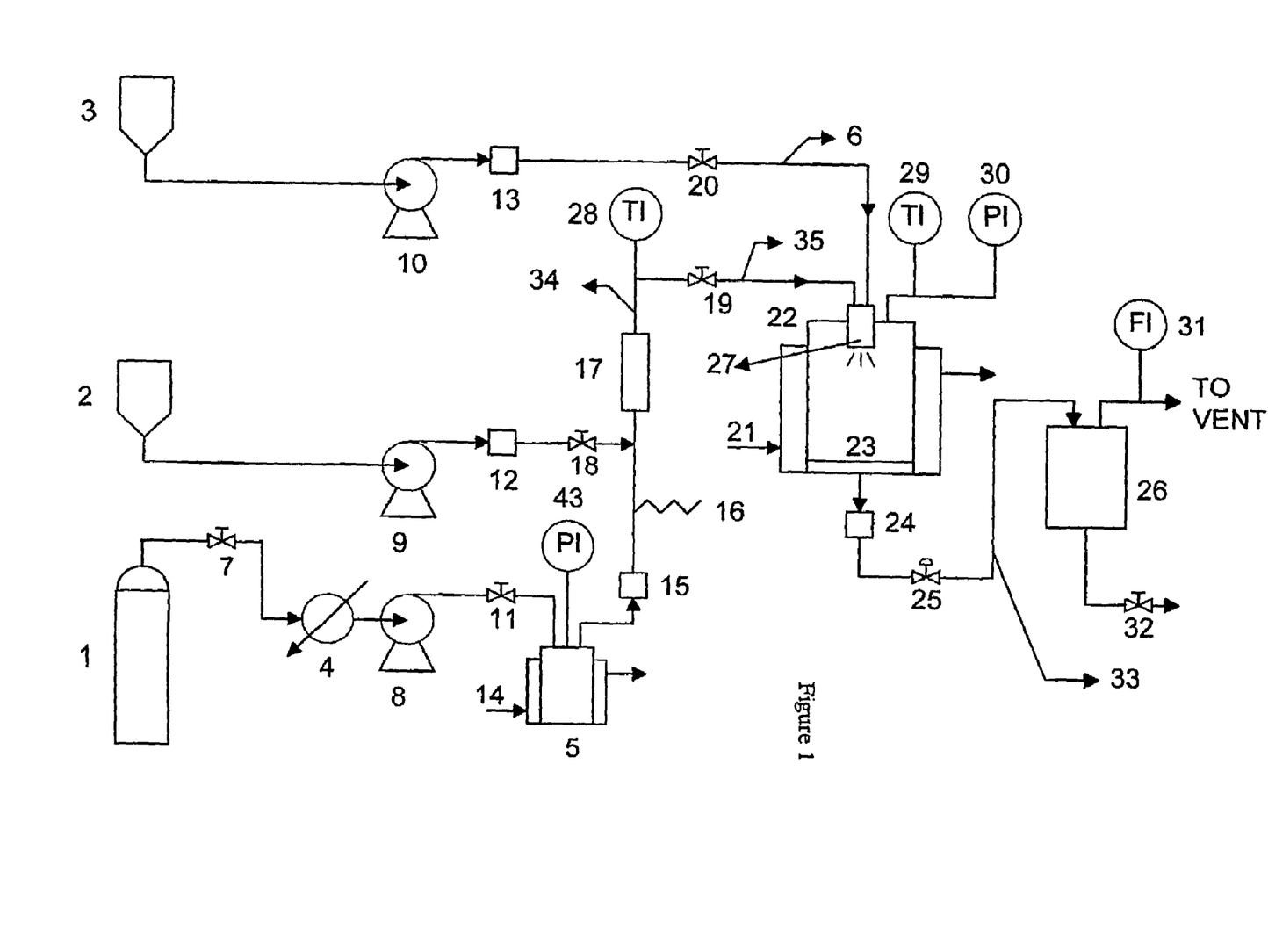
FIG. 1 shows a schematic flow sheet of the apparatus used to carry out the process according to this invention.
Figure 2:
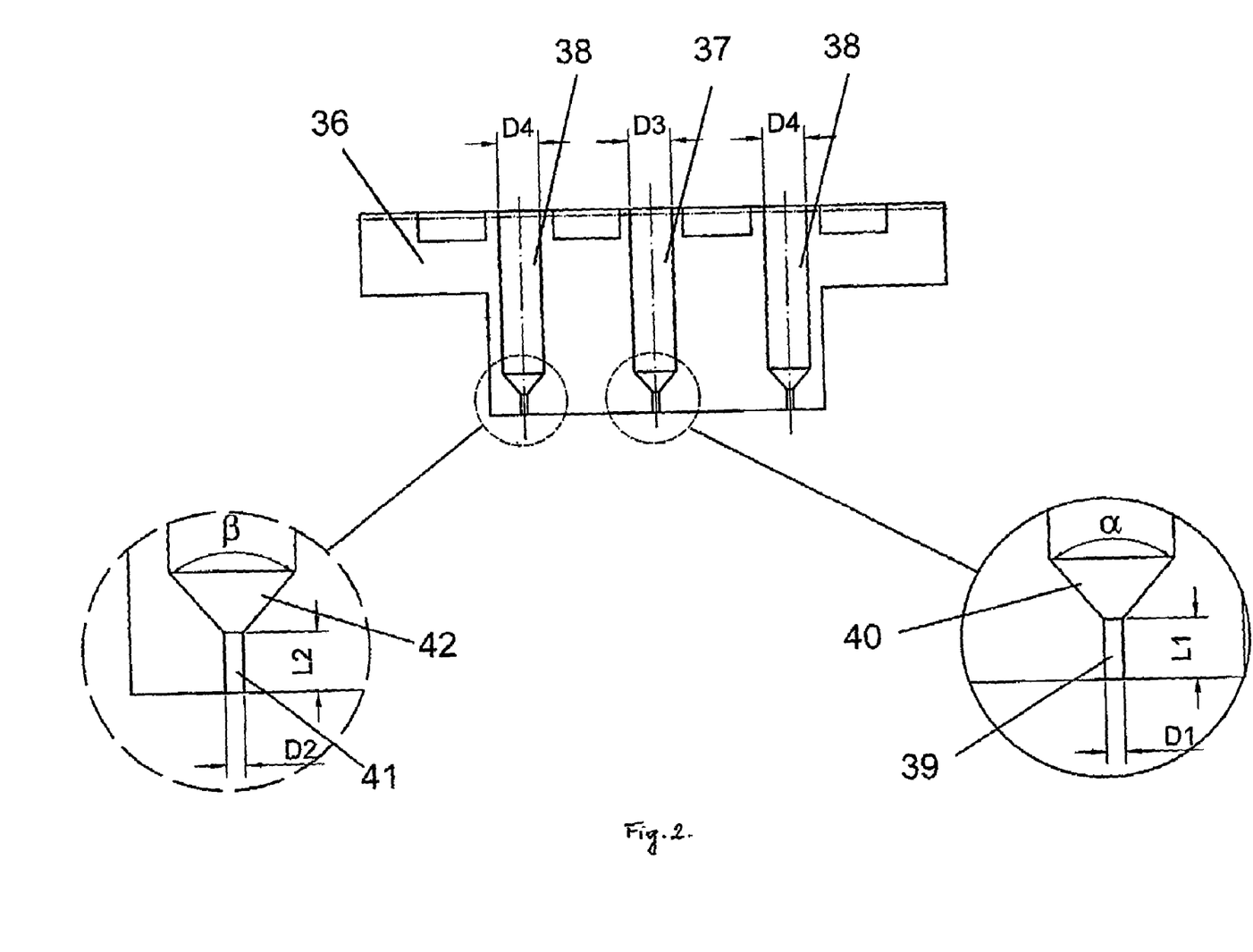
FIGS. 2 and 3 show the nozzle that is used to carry out the process according to this invention.
Figure 3:
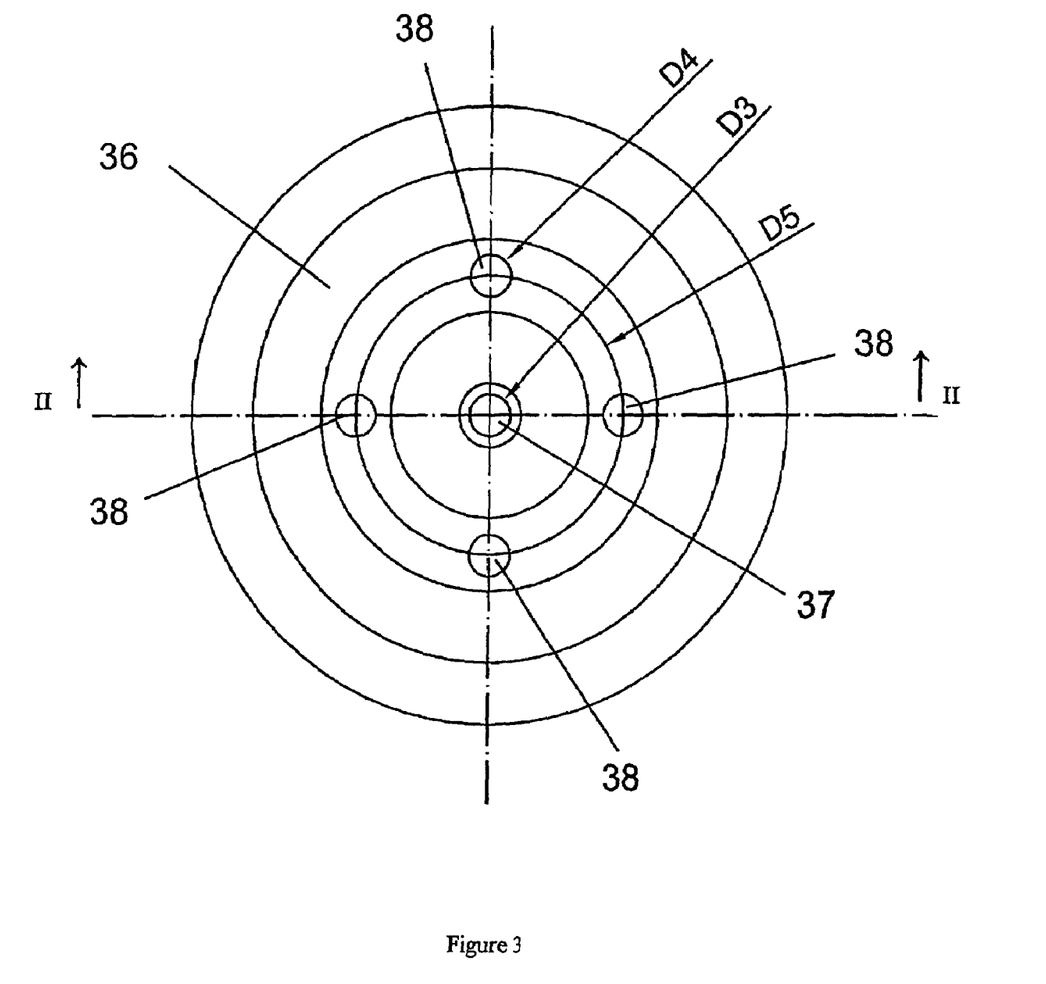

More preferably, the apparatus in FIG. 1 is used. In this case, the solution of substance and stabiliser, the supercritical fluid and the modifier, if needed, are separately introduced into the particle formation vessel in co-current flow by the nozzle 27. Such a nozzle WO02/68107, which is shown in FIGS. 2 and 3, provides separate inlets for supercritical fluid and solution. In fact, this is a disk with an orifice at its center and two or more orifices at the same distance from the center and evenly spaced along a circumference. All the orifices communicate with the interior of the particle formation vessel. The solution is introduced into the particle formation vessel through the central orifice, while the supercritical fluid, pure or with the modifier, is introduced through the outer orifices.

The modifier and the supercritical fluid are mixed before the introduction into the particle formation vessel. In another version of the process the modifier is introduced into the particle formation vessel in part with the solution and in part with the supercritical fluid or with the solution only.

The substance is preferably a protein or polypeptide compound of pharmaceutical or diagnostic interest, soluble in the solvent and in the mixture solvent/modifier and substantially insoluble in the supercritical fluid.

The stabiliser is preferably a pharmaceutical excipient which is able to stabilise the substance in the co-precipitated product. The stabiliser is soluble in the solvent and in the mixture solvent/modifier and substantially insoluble in the supercritical fluid. Preferably, the stabilizer is a sugar and more preferably is trehalose. A mixture of stabilizers may also be employed.

The solvent is preferably selected from water, ethanol, methanol, DMSO, isopropanol, acetone, THF, acetic acid, ethyleneglycol, polyethyleneglycol and N,N-dimethylaniline. Most preferably the solvent is water.

The supercritical fluid is preferably selected from carbon dioxide, ethane, ethylene, propane, sulfur hexafluoride, nitrous oxide, chlorotrifluoromethane, monofluoromethane, xenon and their mixtures, most preferably carbon dioxide.

The modifier is preferably selected from ethanol, methanol, DMSO, isopropanol, acetone, THF, acetic acid, ethyleneglycol, polyethyleneglycol and N,N-dimethylaniline or mixtures thereof. Most preferably the modifier is ethanol. The modifier and solvent must of course be different.

DETAILED DESCRIPTION OF THE INVENTION

The invention will be described further with particular reference to the substance being a protein. It has been found that it is possible to produce stable dry protein/stabilizer micro-particles through the use of supercritical fluids, using various stabilisers such as carbohydrates, aminoacids and surfactant polymers.

Surprisingly, it has been found that co-precipitation using supercritical fluids allows particular intimate interactions between protein and stabiliser molecules and that for each protein/stabiliser couple there is an optimal weight ratio. If the amount of stabiliser exceeds the optimal amount, the excess does not directly interact with the protein but rather forms particles of pure stabiliser. This behaviour has been evidenced by Microscopy and by Differential Scanning Calorimetry (DSC) analysis.

The process for the co-precipitation of a substance with a stabiliser by a GAS process comprising the use of a supercritical fluid pure or mixed with a modifier and a solution into a particle formation vessel may be carried out by the apparatus reported in Figure.

An advantage of the apparatus in FIG. 1 is related to the contact between supercritical fluid and solution since this takes place only in the particle formation vessel. Hence any powder precipitation cannot occur inside the nozzle and cause blockage. Importantly the supercritical fluid acts as an anti-solvent but also promotes conversion of the solution into a fine spray as it enters the particle formation vessel. This widens the solution/anti-solvent interface and permits a more rapid mixing of the two phases and hence a rapid protein precipitation without any denaturation. In addition, the enhancement of mass transfer rate between solution and supercritical fluid allows operation at mild temperature and pressure conditions which contribute to the avoidance of any possible protein denaturation. The apparatus of FIG. 1 includes a particle formation vessel 22. This is a standard reaction vessel of an appropriate volume. The temperature in the vessel is maintained constant by means of a heating jacket 21. The pressure in the vessel is controlled by means of a micro metering valve 25.

The temperature and pressure in the particle formation vessel are measured by means of a thermocouple 29 and a pressure transducer 30.

The particles formed are retained by filter 23. This is a stainless steel basket, whose bottom is made by a sintered stainless steel disk (0.5 µm). A second filter 24 (0.5 µm) is put at the vessel outlet.

The supercritical fluid is withdrawn from cylinder 3, it is condensed by cooler 4 and pumped by means of pump 8 to the particle formation vessel through line 34. Prior to entry into the particle formation vessel, the supercritical fluid is heated to the desired temperature by means of pre-heater 14 and heater 17. The pre-heater 14 also acts as pulsation damper. The supercritical fluid is also filtered by means of filter 15 (0.5 µm). Temperature and pressure of the supercritical fluid prior entry into the precipitation vessel are measured by means of thermocouple 29 and pressure transducer 30, respectively.

The modifier is withdrawn from tank 2, it is pumped by means of pump 9 to line 34 and it is mixed with the supercritical fluid prior to entry into the particle formation vessel. The modifier is also filtered by means of filter 12 (0.5 µm).

Line 34 is equipped with a relief valve 16.

The solution is withdrawn from tank 1, it is pumped by means of pump 10 to the particle formation vessel through line 36. The solution is also filtered by means of filter 13 (0.5 µm).

In another version of the process, the modifier may be introduced into the particle formation vessel in part with the solution and in part with the supercritical fluid. The supercritical fluid, pure or mixed with the modifier, and the solution are fed into the particle formation vessel by means of the nozzle 27.

Downstream the precipitation vessel 22, the mixture of supercritical fluid, modifier and solvent are filtered by means of the filter 24 (0.5 µm) to retain the particles that are eventually not retained by filter 23. The mixture of supercritical fluid, modifier and solvent is depressurised by means of micro metering valve 25, the supercritical solvent is separated from the modifier and the solvent in the separator 26, its flow rate is measured by means of mass flow meter 31 and it is discharged.

The nozzle which is shown in FIGS. 2 and 3 allows introduction of the solution and the supercritical fluid, pure or mixed with the modifier, into the particle formation vessel in co-current flow. The solution and supercritical fluid velocities at the nozzle outlet are related to the mass flow rate and to the diameter of orifices. Moreover, it is preferred that the energy pressure of both solution and supercritical fluid are converted into kinetic energy with a minimum energy loss. The nozzle of FIGS. 2 and 3 was, in fact, designed for this purpose. The peculiarity of this nozzle is that the expansion of solution and supercritical fluid occurs through orifices. An orifice is characterized by a length to diameter ratio ranging from 5 to 10. It has the advantage over the capillary of minimizing the pressure energy loss and of efficiently converting the pressure energy into kinetic energy. The nozzle has orifices with diameters ranging from 0.02 to 0.04 mm and length ranging from 0.1 to 0.2 mm. Such dimensions allow very high velocities at the orifice outlet for both solution and supercritical fluid.

The nozzle may be made of stainless steel, or of other appropriate material.

The nozzle is a disk with an orifice 39 at its centre and two or more orifices 41 drilled at the same distance from the centre and evenly spaced along a circumference. The orifices communicate with the interior of the particle formation vessel. The solution is introduced into the particle formation vessel through the central orifice, the supercritical fluid, pure or with the modifier, is introduced into the particle formation vessel through the outer orifices. The solution 37 passes through a passage of diameter D3. Its end has a conical shape 40. At the apex of the conical end 40 there is a laser drilled orifice 39. The length L1 of the central orifice is 5 to 10 times its diameter D1. The diameter D1 can be chosen in such a way to obtain any desired velocity of the solution at the orifice outlet.

The supercritical fluid 38 passes through passages of diameter D4. Each passage end has a conical shape 42. At the apex of the conical end 42 there is a laser drilled orifice 41. The length 21 of the orifice is 5 to 10 times its diameter D2. The diameter D2 can be chosen in such a way to obtain any desired velocity of the supercritical fluid at the orifice outlet.

The ratio between length (L1 or L2) and diameter (D1 or D2) of the orifices 39 and 41 are chosen so as to set to a minimum the energy loss and to obtain higher velocities by converting energy pressure into kinetic energy.

The solution emerges from the central orifice 39 at high velocity and it is broken in fine droplets coming in contact with the supercritical fluid. The dispersion of the solution liquid jet is enhanced by the supercritical fluid emerging from orifices 41, provided that the supercritical fluid velocity is very high, of the order of magnitude of the velocity of sound at the working temperature and pressure. The effect of the supercritical fluid in enhancing the dispersion of the solution liquid jet is crucial and determines the shape, size and yield of the product.

Orifices can be drilled with diameters down to 0.02 mm. The nozzles that have been used for carrying out the tests have orifices of diameter ranging from 0.02 to 0.04 mm. In another embodiment of the invention, one or more of the outer orifices are drilled in such a way that their axes converge on the axis of the central orifice. The angle formed by the axis of the outer orifices with the axis of the central orifice is between 1 and 30°.

A crucial point in the process for fine dry protein microparticle formation is the mixing of the solution with the supercritical fluid: a rapid and intimate mixing causes precipitation of particles with a small diameter and enables a high powder yield.

In order to have a good mixing, the solution should be dispersed into the supercritical fluid in form of small droplets, thus providing high interfacial area for mass transfer and a short path for the diffusion of supercritical fluid in the solution droplets and thereby preventing the growth of solute particles. Moreover a high ratio between flow rate of supercritical fluid and flow rate of solution causes a large excess of the supercritical fluid to solution at the moment of their contact, enhancing the driving force for mass transfer of the supercritical fluid into the solution and of solvent into supercritical fluid.

When the solvent solubility in the supercritical fluid is low, the use of a modifier allows a better mixing between solution and supercritical fluid.

When a modifier is used, the ratio of modifier flow rate and of solution flow rate has to be chosen so that a high increase in solubility of solvent in the supercritical fluid is obtained. The modifier can be introduced with the supercritical fluid or with the solution or in part with the supercritical fluid and in part with the solution. The way of introduction of the modifier greatly influences the extraction of the solvent and the structure of particles that are formed.

For the precipitation of powders from aqueous solution using carbon dioxide as supercritical solvent and ethanol as modifier the ratio between supercritical fluid flow rate and modifier flow rate is preferably within the range 4-8, more preferably 7, while the ratio between modifier flow rate and the solution flow rate is preferably within the range 15-25 and more preferably 20.

As pointed out above, it is necessary to have a good dispersion of the solution into the supercritical fluid in order to obtain very small droplets of solution.

The size of the formed solution droplets is determined by the fluidodynamic conditions in the mixing zone and by the physical properties of solution and supercritical solvent, such as viscosity, surface tension, density. These properties are greatly influenced by the temperature and pressure of the supercritical fluid.

The supercritical fluid inlets are positioned around the solution inlet and at a very short distance therefrom (about 3 mm): this configuration allows the solution to be energized by the supercritical fluid thus enhancing the dispersion of the solution into very fine droplets, providing high interfacial surface are between the two phases and fast extraction of solvent into supercritical fluid. These phenomena are particularly efficient when the supercritical fluid velocity at the orifice outlet reaches or is greater than the speed of sound causing a Mach disc formation and solution dispersion as very fine droplets (Matson D. W., Fulton J. L., Petersen R. C., Smith R. D., "*Rapid expansion of supercritical fluid solutions: solute formation of powders, thin films, and fibers*" Ind. Eng. Chem. Res., 1987 26, 2298-2306). The speed of sound in a fluid is strongly dependent on pressure and temperature: the minimum value of speed of sound for carbon dioxide in the supercritical region is 208 m/s at 8 MPa and 40° C. To take advantage of the above mentioned phenomena it is convenient to work around the value of speed of sound for carbon dioxide in the supercritical region, e.g. 208 m/s at 8 MPa and 40° C.

For the production of fine powders from aqueous solutions with the GAS process using carbon dioxide as supercritical solvent and ethanol as modifier, it was found that optimal operative conditions are 8-12 Mpa and 35-50° C. In the experimental apparatus used for carrying out the experimental tests, the supercritical fluid mass flow rate was 30 g/min, the solution flow rate 0.2 g/min, and the modifier mass flow rate 4 g/min, having set the ratio of supercritical fluid to modifier mass flow rate at 7 and the ratio of modifier to solution mass flow rate at 20 and supercritical fluid velocity at the nozzle outlet at about 300 m/s. Using this apparatus we carried out the process to produce stable dry micro-particles of a substance and a stabiliser by GAS co-precipitation. Proteins such as Alkaline Phosphatase and Lysozyme were used as the substance and Trehalose as stabiliser. Co-precipitated powders at different protein/stabiliser ratio were produced. The yield of the collected powder was 90%. The retained enzymatic activity after the process was found to be within 95% and 100%, compared to the unprocessed commercial reagent. The particle size distributions of these powders showed that more than 90% of the particles have an equivalent diameter less then 10 μm with a narrow size distribution. Furthermore, the physicochemical characterisation showed that co-precipitation allows intimate interactions between protein and stabiliser molecules and for each protein/stabiliser couple there is an optimal weight/weight ratio. Finally, stability studies showed that the Alkaline phosphatase/trehalose co-precipitated particles were more stable than the equivalent freeze-dried product.

Experimental Procedure

The supercritical fluid is fed to the precipitation vessel by means of pump 8, which is used to set the supercritical fluid flow rate. The temperature of the supercritical fluid in line 35 is set by means of heater 17 to a higher value than the temperature inside the particle formation vessel, to take into account the temperature lowering due to the expansion through the nozzle orifices. The modifier is then added at a predetermined flow rate to the supercritical fluid by means of pump 9. The solution of protein and stabiliser is pumped by means of pump 10 into the particle formation vessel when steady state conditions are attained.

After that a certain amount of solution is fed into the particle formation vessel, pumps 9 and 10 are stopped and only the supercritical fluid is fed to the particle formation vessel as long as the precipitated powder is free of solvent and modifier.

The particle formation vessel is depressurised, the powder is recovered and sealed in 10 mL vials under dry nitrogen.

The co-precipitated proteins stability was tested by storing vials at the following conditions: 25° C.-60% RH; 30° C.-65% RH; 40° C.-75% RH. Each sample was analysed for biological activity at t=0, 1, 2, 3 and 6 months. As comparison, a parallel study was conducted on protein precipitated by supercritical fluids as is, on analogous freeze-dried products and on the unprocessed commercial product, all stored under dry nitrogen.

EXAMPLE 1

Preparation of Alkaline Phosphatase (ALP)/Trehalose Co-Precipitate Particles

In this example, the method of the invention is used to co-precipitate mixtures of alkaline phosphatase (ALP) and trehalose.

Solutions containing ALP (SIGMA Chemicals) at concentration 0.2% w/w and trehalose (SIGMA Chemicals) at concentration within the range 0-2% w/w in deionized water were used.

The ALP/Trehalose ratios of the obtained powders were as follow: 1:10, 1:2 and 1:0. Carbon dioxide as supercritical fluid and ethanol as modifier were used.

The solution was fed into the particle formation vessel 22 by means of pump 10 at a flow rate of 0.2 g/min. Supercritical carbon dioxide was fed by means of pump 8 at a flow rate of 30 g/min, ethanol was fed by means of pump 9 to line 34 at a flow rate of 4 g/min and it was mixed with supercritical carbon dioxide prior to entry into the particle formation vessel.

The supercritical fluid was injected into the particle formation vessel through the four external orifices of the nozzle, each with a diameter of 0.04 mm. The solution was injected into the particle formation vessel through the central orifice of the nozzle, having a diameter of 0.04 mm. The length of all orifices was 0.2 mm.

Temperature and pressure inside the particle formation vessel were maintained at a constant 40° C., by means of the heating jacket 21, and 100±1 bar by means of the micro metering regulation valve 25, respectively. Precipitated particles were collected on the filter 23 at the bottom of particle formation vessel, while supercritical fluid, modifier and water were collected into the cylinder 26 at atmospheric pressure.

The process was conducted as long as a sufficient amount of powder was obtained. After the solution and modifier feeds were stopped and only pure carbon dioxide was fed into particles formation vessel in order to extract any trace of solvent and modifier from the precipitated powders. Typically, the particle formation vessel was washed with two volumes of carbon dioxide in order to obtain dry powders.

After depressurisation, the particle formation vessel was opened and the powders were recovered and stored in 10 mL vials under dry nitrogen.

The yield of the collected powder was 90%.

The residual enzymatic activity of ALP was within 95% and 100%, compared to the unprocessed commercial reagent. The powder optical microscopy analysis shows that at high trehalose content as for ALP/trehalose ratio 1:10 the powder is formed by two different population of particles: one, which is the largely frequent, is formed by needle shaped particles, while the other by round shaped particles. The needle shaped particles are quite similar to those obtained by trehalose as is precipitation by supercritical $CO_2$. The lower trehalose content powders show the round shaped particles population only. Thus, the trehalose can be co-precipitated with ALP by supercritical $CO_2$ to give one kind of particles only at the lower trehalose contents (protein/trehalose ratios 1:2). Similar behaviour was found for lysozyme/trehalose co-precipitates (see example 2). Analogous products were prepared by freeze-drying. In this case the found residual enzymatic activity of ALP was within 95% and 104%, compared to the unprocessed commercial reagent.

Similar vials containing unprocessed commercial ALP or analogous freeze-dried products, all under dry nitrogen, were prepared.

Stability Study

Several vials of each category were placed at each of the following conditions: 25° C.-60% RH; 30° C.-65% RH; 40° C.-75% RH for 6 months. At t=0, 1, 2, 3, 6 months, the contents of the vials were assayed for ALP activity. The stability studies results are summarised in Table 1.

Pure ALP precipitated by supercritical $CO_2$ (sample F6) shows a decay of enzymatic activity at all the conditions. The residual activity after 6 months at 40° C.-75% RH (most extreme conditions), is 57% of the t=0 value.

On the contrary, no significant loss of activity at all conditions up to 6 months was found for ALP/trehalose co-precipitated by supercritical $CO_2$ at ratio 1:10 (sample FT8).

At 40° C.-75% RH, pure freeze-dried ALP (sample F8) and SIGMA commercial product show similar decays and only 43% and 42% of the initial enzymatic activity was retained after 6 months. At the other conditions, instead, the SIGMA product shows a slower activity loss than the pure freeze-dried ALP. In fact after 6 months the following residual enzymatic activity were detected: 95% vs 83% at 25° C.-60% RH, and 86% vs 76% at 30° C.-65% RH.

Finally, the freeze dried powder having the ALP/trehalose ratio of 1:10 (sample FT10) showed an initial rapid loss of activity, then a slower one up to six months which seams to be independent to the storage conditions. In fact the retained enzymatic activities at 250° C.-60% RH, 30° C.-65% RH and 40° C.-75% are 90%, 88% and 90% respectively of the initial value.

EXAMPLE 2

Preparation of Lysozyme/Trehalose Co-Precipitate Particles

In this example, the method of the invention is used to prepare co-precipitate powders using lysozyme and trehalose.

Solutions containing lysozyme (SIGMA Chemicals) at concentration within 0.2-1% w/w and trehalose (SIGMA Chemicals) at concentration within the range 0-2% w/w in deionized water were used. The lysozyme/trehalose ratios of the obtained powders were as follows: 1:10, 1:5, 1:2, 1:1, 2:1, 4:1 and 1:0 (Table 2).

Carbon dioxide was used as supercritical fluid and ethanol as modifier.

The aqueous solution containing the enzyme and the stabiliser was fed into the particle formation vessel 22 by means of pump 10 at a flow rate of 0.2 g/min. Supercritical carbon dioxide was fed by means of pump 8 at a flow rate of 30 g/min, ethanol was fed by means of pump 9 to line 34 at a flow rate of 4 g/min and it was mixed with supercritical carbon dioxide before entering into the particle formation vessel.

The supercritical fluid was injected into the particle formation vessel through the four external orifices of the nozzle, each with a diameter of 0.04 mm. The solution was injected into the particle formation vessel through the central orifice of the nozzle, having a diameter of 0.04 mm. Length of all orifices is 0.2 mm.

Temperature and pressure inside the particle formation vessel were maintained at a constant 40° C., by means of the heating jacket 21, and 100±1 bar by means of the micro metering regulation valve 25, respectively.

Precipitated particles were collected on the filter 23 at the bottom of particle formation vessel, while supercritical fluid, modifier, water and solute eventually not precipitated were collected in the cylinder 26 at atmospheric pressure.

After that, a certain amount of solute was fed into the particle formation vessel, pumps 9 and 10 were stopped and only supercritical fluid was fed into the particle formation vessel in order to dry the precipitated powders: typically, it requires about two times the volume of the particles formation vessel to obtain dry powders.

At this point, the particle formation vessel was depressurised, opened and the powders collected.

The yield of recovered powders was 90%.

The found residual enzymatic activity of lysozyme was within 96% and 100%, compared to the unprocessed commercial reagent.

Table 2 reports for each sample the lysozyme/trehalose ratio, the retained enzymatic activity, the protein content which is related to homogeneity of precipitation, the number of particles populations and the particle sizes. As can be noted, for all the samples, both enzymatic activity and protein content are very close to theoretical values. Thus the experimental conditions we used allowed a similar precipitation for both protein and sugar and guaranteed an almost complete biological activity recovery.

Figure 4:
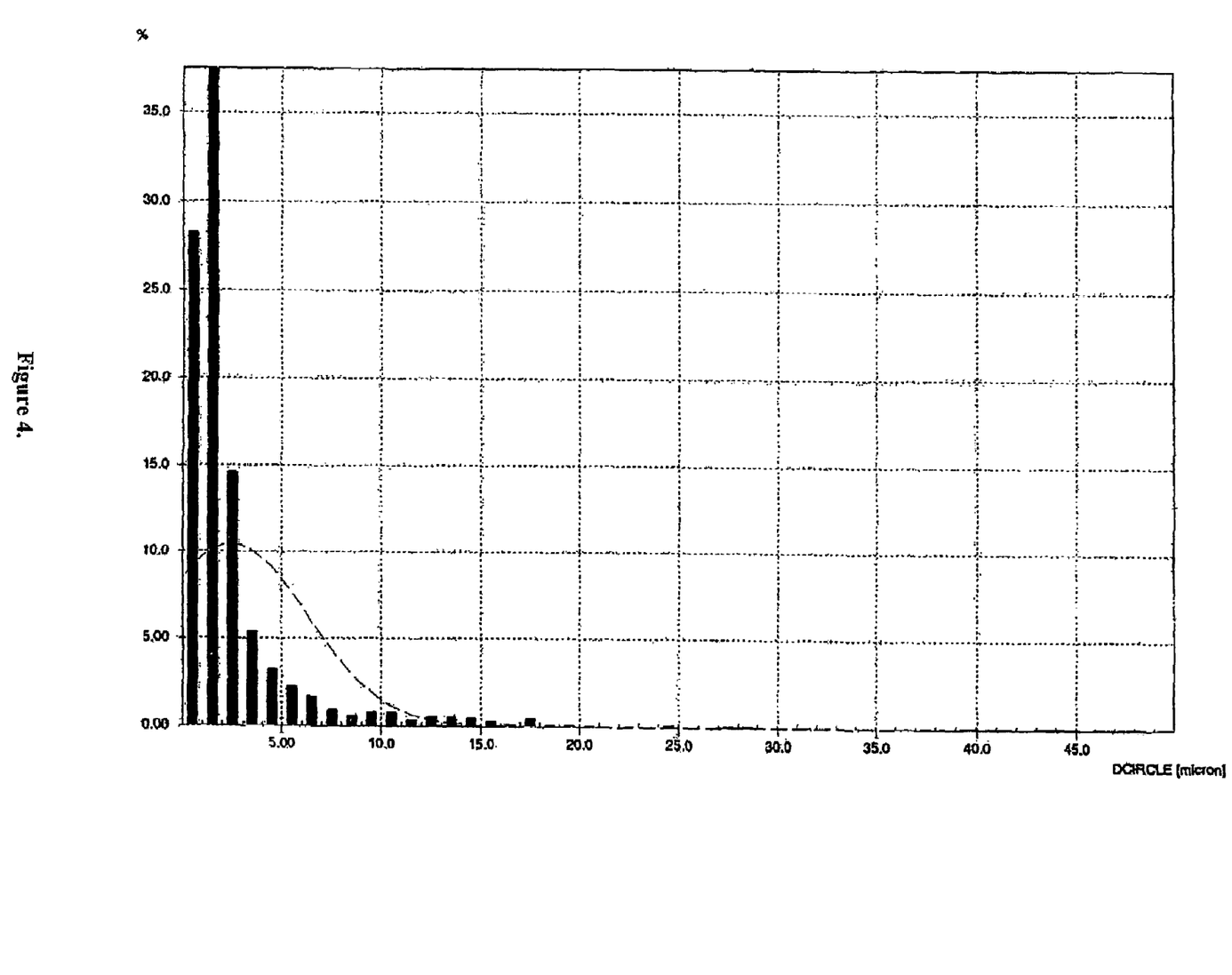
FIGS. 4, 5 and 6 show the particle size distributions of supercritical $CO_2$ co-precipitated lysozyme/trehalose powders at the w/w ratios 1:10, 1:2 and 1:0 respectively.
Figure 5:
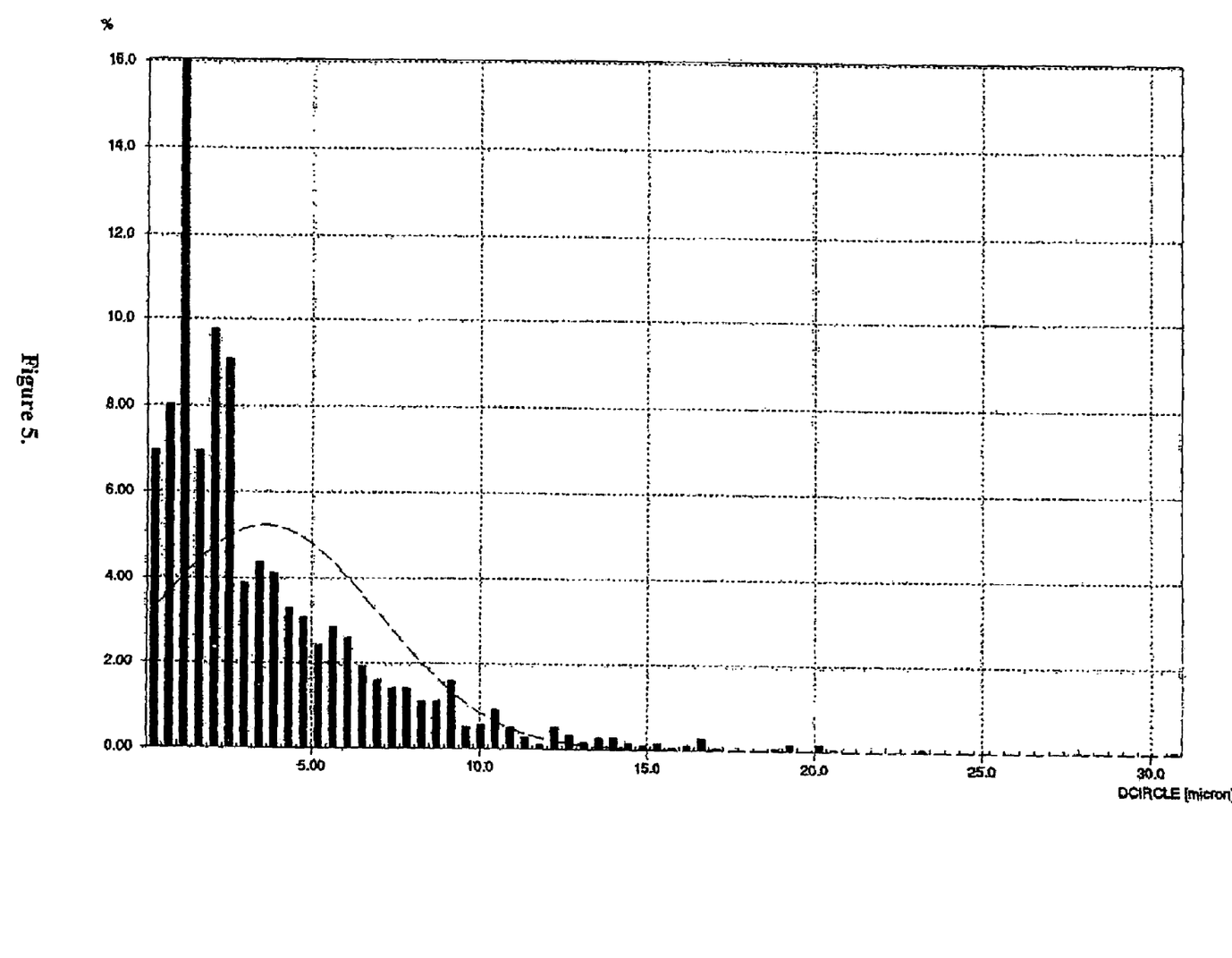
Figure 6:
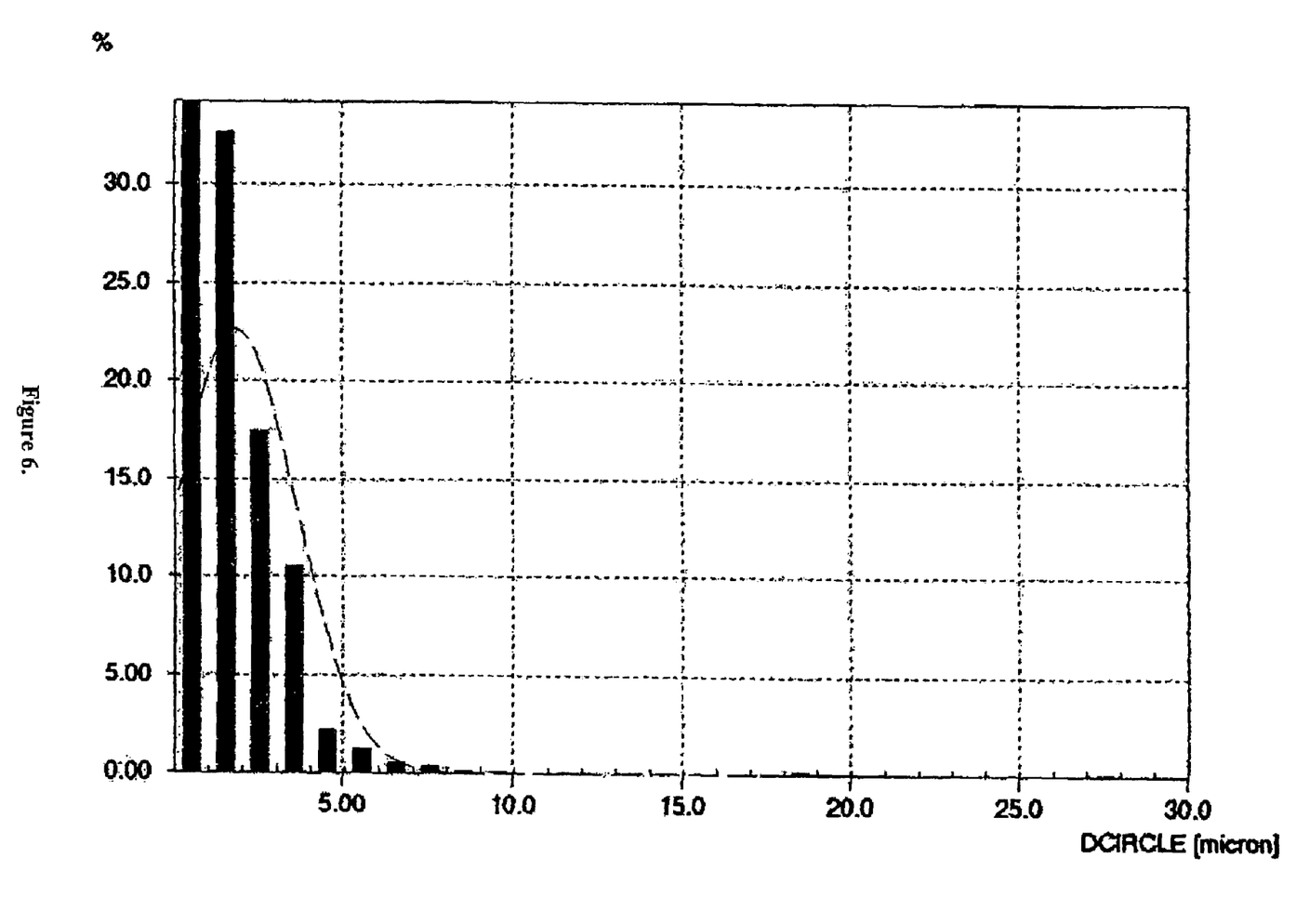
Figure 7:
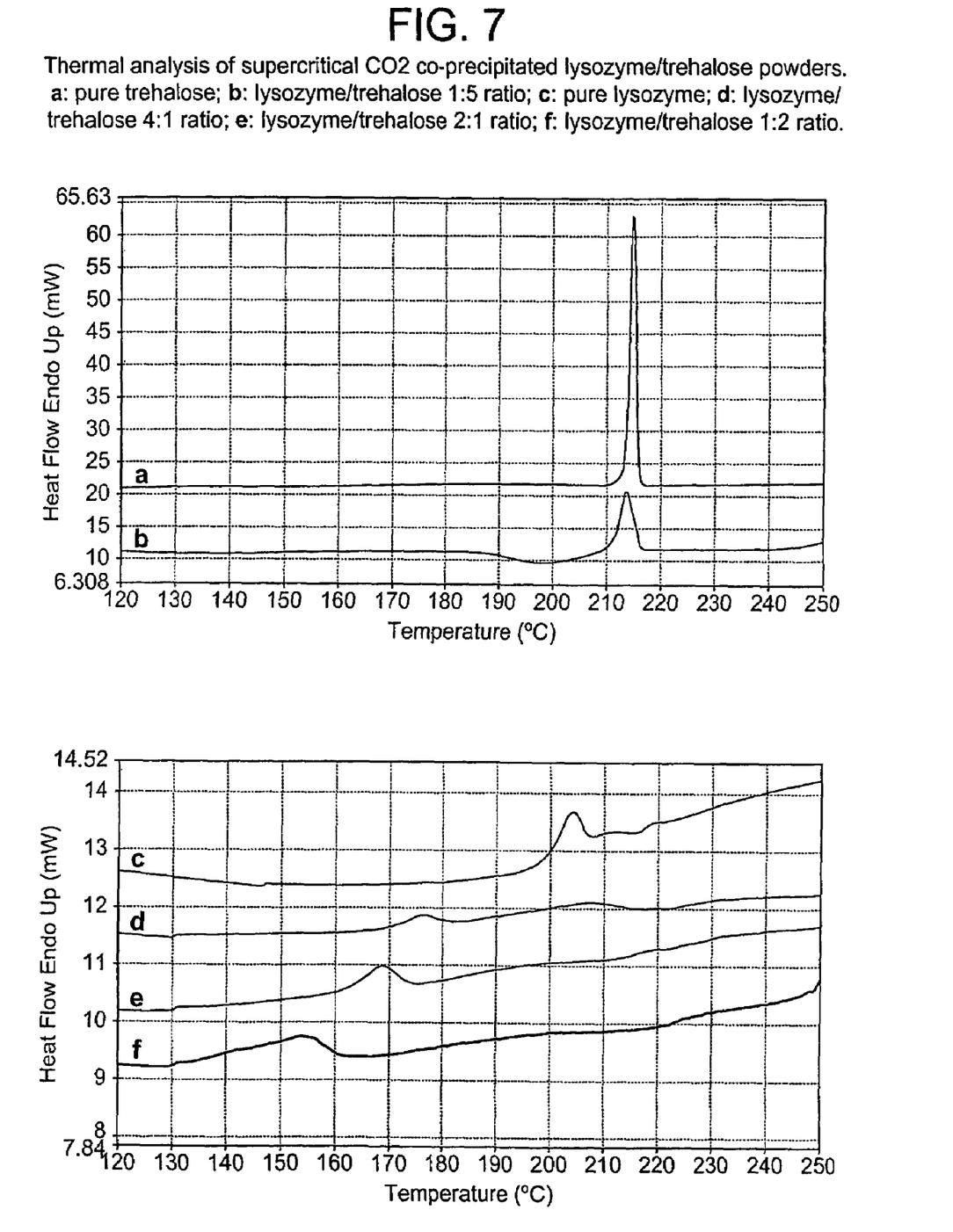
FIG. 7 shows the thermograms obtained by differential scanning calorimetry (DSC) of supercritical $CO_2$ co-precipitated lysozyme/trehalose powders vs the respective pure products.

The particle size distributions of powders calculated by image analysis of SEM micrographs showed that for all the powders obtained by supercritical $CO_2$ precipitation, more than 90% of the particles have an equivalent diameter less then 10 μm with a narrow size distribution. FIGS. 4, 5, 6 show the particle size distributions of supercritical $CO_2$ co-precipitated with lysozyme/trehalose ratios 1:10, 1:2 and 1:0 respectively. The other co-precipitates yielded similar distributions. Moreover, the powders observation by optical microscopy analysis showed that at high trehalose contents as for both lysozyme/trehalose ratios 1:10 and 1:5, the powders were composed of two particle populations: the one, which largely was the most frequent, was formed by needle shaped particles, the other was formed by round shaped particles. The needle shaped particles were quite similar to those obtained by trehalose as precipitated by supercritical $CO_2$. On the contrary, at the lower trehalose content (lysozyme/trehalose ratio 1:2) the powders showed the round shaped particles population only. Thus lysozyme can be co-precipitated with trehalose by supercritical $CO_2$ to form only one kind of particle at the lower trehalose content (higher protein/trehalose ratios). Hence an optimal value for protein/trehalose ratio which guarantees the best interaction between the two kind of molecules exists. This behaviour has been confirmed by DSC analysis. FIG. 7 shows DSC thermograms of various co-precipitated lysozyme powders. As reference, pure precipitated lysozyme and trehalose are also reported. As can be noted, at higher trehalose content (ratio 1:5), samples contain amorphous trehalose which recovers the crystalline abit (exothermic peak at 197° C.) and then melts at 214° C. in the same way of precipitated trehalose itself. The thermal behaviour of lower content trehalose samples is quite different. The samples with ratios 1:2 to 4:1 show thermograms similar to the one of lysozyme as is. The most relevant difference is the shift towards lower temperatures of the characteristic transition of lysozyme at T=204° C. The higher the trehalose content the lower the temperature of transition. Thus, we have strong evidence that co-precipitation by supercritical fluids allows an intimate interaction between protein and trehalose. In fact up to a defined amount of sugar (1:2 ratio) we obtained a homogeneous solid phase. This ratio is able to provide the best protein/sugar interaction and the best long term stability of protein.

TABLE 1

| Sample/ drying method | ALP/ Trehalose Ratio | Storage condition | Enz. Activity at 1 month (% of t = 0) | Enz. Activity at 2 months (% of t = 0) | Enz. Activity at 3 months (% of t = 0) | Enz. Activity at 6 months (% of t = 0) |
|---|---|---|---|---|---|---|
| ALP | 1:0 | −20° C. | — | — | — | 96 |
| Sigma | | 25° C./60% RH | 101 | 100 | 101 | 95 |
| Freeze-drying | | 30° C./70% RH | 103 | 103 | 94 | 86 |
| | | 40° C./75% RH | 94 | 85 | 75 | 42 |
| ALP F6 | 1:0 | −20° C. | — | — | — | — |
| SCF | | 25° C./60% RH | 91 | 72 | 69 | 67 |
| | | 30° C./70% RH | 101 | 71 | 59 | 59 |
| | | 40° C./75% RH | 64 | 69 | 58 | 57 |
| ALP F8 | 1:0 | −20° C. | — | — | — | — |
| Freeze-drying | | 25° C./60% RH | 88 | 89 | 89 | 83 |
| | | 30° C./70% RH | 83 | 87 | 87 | 76 |
| | | 40° C./75% RH | 75 | 75 | 62 | 43 |
| ALP FT8 | 1:10 | −20° C. | — | — | — | 101 |
| SCF | | 25° C./60% RH | 111 | 99 | 113 | 99 |
| | | 30° C./70% RH | 104 | 97 | 102 | 99 |
| | | 40° C./75% RH | 113 | 98 | 101 | 99 |

TABLE 1-continued

| Sample/ drying method | ALP/ Trehalose Ratio | Storage condition | Enz. Activity at 1 month (% of t = 0) | Enz. Activity at 2 months (% of t = 0) | Enz. Activity at 3 months (% of t = 0) | Enz. Activity at 6 months (% of t = 0) |
|---|---|---|---|---|---|---|
| ALP FT10 Freeze- drying | 1:10 | −20° C. | — | — | — | 95 |
|  |  | 25° C./60% RH | 95 | 95 | 93 | 90 |
|  |  | 30° C./70% RH | 94 | 96 | 92 | 88 |
|  |  | 40° C./75% RH | 94 | 93 | 92 | 90 |

TABLE 2

| SAMPLE | Lysozyme I Trehalose Ratio | Enz. Activity (mg Enz.Img Prot.) | Protein content (% on nominal) | No. of particles populations | Particles size (% < 10 jim) |
|---|---|---|---|---|---|
| L3 | 1:0 | 0.96 | 102.6 | 1 | 99 |
| LT2 | 1:10 | 1.04 | 104.3 | 2 | — |
| LT3 | 1:1 | 0.96 | 100.8 | 1 | 98 |
| LT6 | 1:5 | 0.96 | 104.0 | 2 | 92 |
| LT8 | 4:1 | 1.01 | 103.2 | 1 | 97 |
| LT9 | 1:2 | 0.98 | 104.0 | 1 | 93 |
| LT10 | 2:1 | 0.97 | 103.9 | 1 | 97 |

The invention claimed is:

1. A process for the co-precipitation of a protein or polypeptide with a stabiliser therefor, by a gas anti solvent process comprising introducing into a particle formation vessel a supercritical fluid pure or mixed with a modifier; and
 a solution comprising said protein or polypeptide and said stabiliser dissolved in a solvent;
 so as said solvent is extracted from the solution by said supercritical fluid and co-precipitation of said protein or polypeptide and stabiliser occurs, wherein said stabiliser is a sugar.

2. A process as claimed in claim 1 wherein the solution comprises the protein and the co-precipitation of the protein and stabiliser occurs.

3. A process as claimed in claim 1 wherein said solution and said supercritical fluid are introduced into said particle formation vessel via separate inlet nozzles.

4. A process according to claim 3 wherein said supercritical fluid is introduced into said particle formation vessel via a plurality of inlet nozzles.

5. A process as claimed in claim 4 wherein said nozzles are present on a disk, the solution inlet nozzle being in the centre of said disk surrounded by a plurality of supercritical fluid inlet nozzles evenly spaced along the circumference thereof.

6. A process according to claim 1, wherein the solution is introduced into the particle formation vessel mixed with a modifier.

7. A process according to claim 1 wherein the supercritical fluid is introduced into the particle formation vessel mixed with a modifier.

8. A process according to claim 1, wherein said supercritical fluid is selected from carbon dioxide, ethane, ethylene, propane, sulfur hexafluoride, nitrous oxide, chlorotrifluoromethane, monofluoromethane, xenon and mixtures thereof.

9. A process according to claim 1, wherein said solvent is selected from water, ethanol, methanol, DMSO, isopropanol, acetone, THF, acetic acid, ethylene glycol, polyethylene glycol and N,N-dimethylaniline and mixtures thereof.

10. A process according to claim 1, wherein said modifier, which is different from said solvent is selected from water, ethanol, methanol, DMSO, isopropanol, acetone, THF, acetic acid, ethylene glycol, polyethylene glycol and N,N-dimethylaniline and mixtures thereof.

11. A process according to claim 1, wherein the supercritical fluid is carbon dioxide, the solvent is water and the modifier is ethanol.

12. A process according to claim 1, wherein the stabiliser is a trehalose.

13. A process according to claim 1 wherein the ratio of protein or polypeptide to stabiliser in the solution is 1:1 to 1:10 w/w.

14. A process according to claim 13 wherein the ratio of protein or polypeptide to stabiliser in the solution is 1:2 w/w.

15. A process as claimed in claim 1 wherein the supercritical fluid enters the particle formation vessel at the speed of sound in the fluid or greater.

16. A process as claimed in claim 1 where a modifier is used and the ratio between supercritical fluid flow rate and modifier flow rate is within the range 4:1 to 8:1 w/w.

17. A process as claimed in claim 1 where a modifier is used and the ratio between modifier flow rate and solution flow rate is within the range 15:1 to 25:1 w/w.

18. A process for the co-precipitation of a protein or polypeptide with a stabiliser therefor, by a gas anti solvent process comprising introducing into a particle formation vessel a supercritical fluid pure or mixed with a modifier; and a solution comprising said protein or polypeptide and said stabiliser dissolved in a solvent; so as said solvent is extracted from the solution by said supercritical fluid and co-precipitation of said protein or polypeptide and stabiliser occurs, wherein said stabiliser is a sugar, wherein the ratio of said protein or said polypeptide to said stabiliser in said solution is from about 1:2 to 4:1 w/w.

* * * * *